US00PP36668P2

(12) United States Plant Patent
Mays

(10) Patent No.: US PP36,668 P2
(45) Date of Patent: May 13, 2025

(54) BOXWOOD PLANT NAMED 'TM108'

(50) Latin Name: *Buxus microphylla*
Varietal Denomination: TM108

(71) Applicant: Saunders Genetics, LLC, Piney River, VA (US)

(72) Inventor: Theodore Mays, Piney River, VA (US)

(73) Assignee: SAUNDERS GENETICS, LLC, Piney River, VA (US)

( * ) Notice: Subject to any disclaimer, the term of this patent is extended or adjusted under 35 U.S.C. 154(b) by 0 days.

(21) Appl. No.: 18/748,357

(22) Filed: Jun. 20, 2024

(51) Int. Cl.
*A01H 5/12* (2018.01)
*A01H 6/00* (2018.01)

(52) U.S. Cl.
USPC ..... Plt./226

(58) Field of Classification Search
USPC ..... Plt./226
CPC ..... A01H 5/12; A01H 5/00; A01H 6/00
See application file for complete search history.

(56) References Cited

U.S. PATENT DOCUMENTS

PP16,052 P2 10/2005 Peerenboom

OTHER PUBLICATIONS

Kiefer Nursery 2023 USDA Plant Hardiness Zone May for North Carolina 2024, retrieved on Sep. 10, 2024 at https://kiefernursery.com/usda-hardiness-zones/, 5 pp. (Year: 2024).*
Saunders, Boxwood Blight—A Managed Disease 2020, retrieved on Sep. 10, 2024 at https://irp.cdn-website.com/5d757b5b/files/uploaded/Boxwood_BlightAManagedDiseas.pdf, 4 pp. (Year: 2020).*

* cited by examiner

*Primary Examiner* — June Hwu
(74) *Attorney, Agent, or Firm* — Panitch Schwarze Belisario & Nadel LLP; Stephany G. Small; Travis W. Bliss

(57) ABSTRACT

A new and distinct variety of boxwood plant, referred to by its cultivar name, 'TM108', is disclosed. The new variety provides bright variegated leaf color, which is retained in the fall and winter, and resists winter foliar bronzing. Very good resistance to boxwood blight (*Calonectria pseudonaviculata*) is exhibited. The growth habit is compact and rounded. The new variety is well suited for providing attractive ornamentation in the landscape.

3 Drawing Sheets

Latin name of genus and species of plant claimed: *Buxus microphylla.*

Variety denomination: 'TM108'.

BACKGROUND OF THE INVENTION

The new variety of boxwood plant was discovered growing in a cultivated area in Albemarle, North Carolina in 2009. The new variety was selected in 2012 as a single limb mutation on an unnamed boxwood plant (not patented) in a display garden during a blight trial. The sport was selected and grown as a single plant of the new variety. Trialing resulted in the new variety showing very good resistance to blight. The parent variety is unknown.

The new variety has been found to undergo asexual propagation by terminal hardwood stem cuttings. Asexual propagation by terminal stem cuttings in Low Gap, North Carolina has shown that the characteristics of the new variety are stable and are strictly transmissible by such asexual propagation from one generation to another. Accordingly, the new variety undergoes asexual propagation in a true-to-type manner.

SUMMARY OF THE INVENTION

It was found that the new variety of boxwood plant of the present invention:

(a) displays bright variegated leaf color, which is retained in the fall and winter,
(b) resists winter foliar bronzing,
(c) exhibits very good resistance to boxwood blight (*Calonectria pseudonaviculata*), and
(d) provides a compact, rounded growth habit.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from similar varieties that are commercially available. The most similar in comparison to the new cultivar is the 'PEERGOLD' variety (U.S. Plant Pat. No. 16,052; GOLDEN DREAM™). The new variety of the present invention can readily be distinguished at least because plants of the new variety have foliage that retains brighter color in the fall and winter compared to plants of the 'PEERGOLD' variety that have foliage that turns orange in the fall and winter due to bronzing.

The new variety has been named 'TM108'.

BRIEF DESCRIPTION OF THE PHOTOGRAPH

The accompanying photographs show as nearly true as it is reasonably possible to make the same, in a color illustration of this character, typical specimens of the plant and plant parts of the new variety. Colors in the photographs may differ slightly from the color values cited in the detailed description, which accurately describes the colors of the 'TM108' variety. The photographed plant was approximately three and a half years old and growing outdoors in Low Gap, North Carolina in 2024 and pruned a couple months prior to picture.

Figure 1:
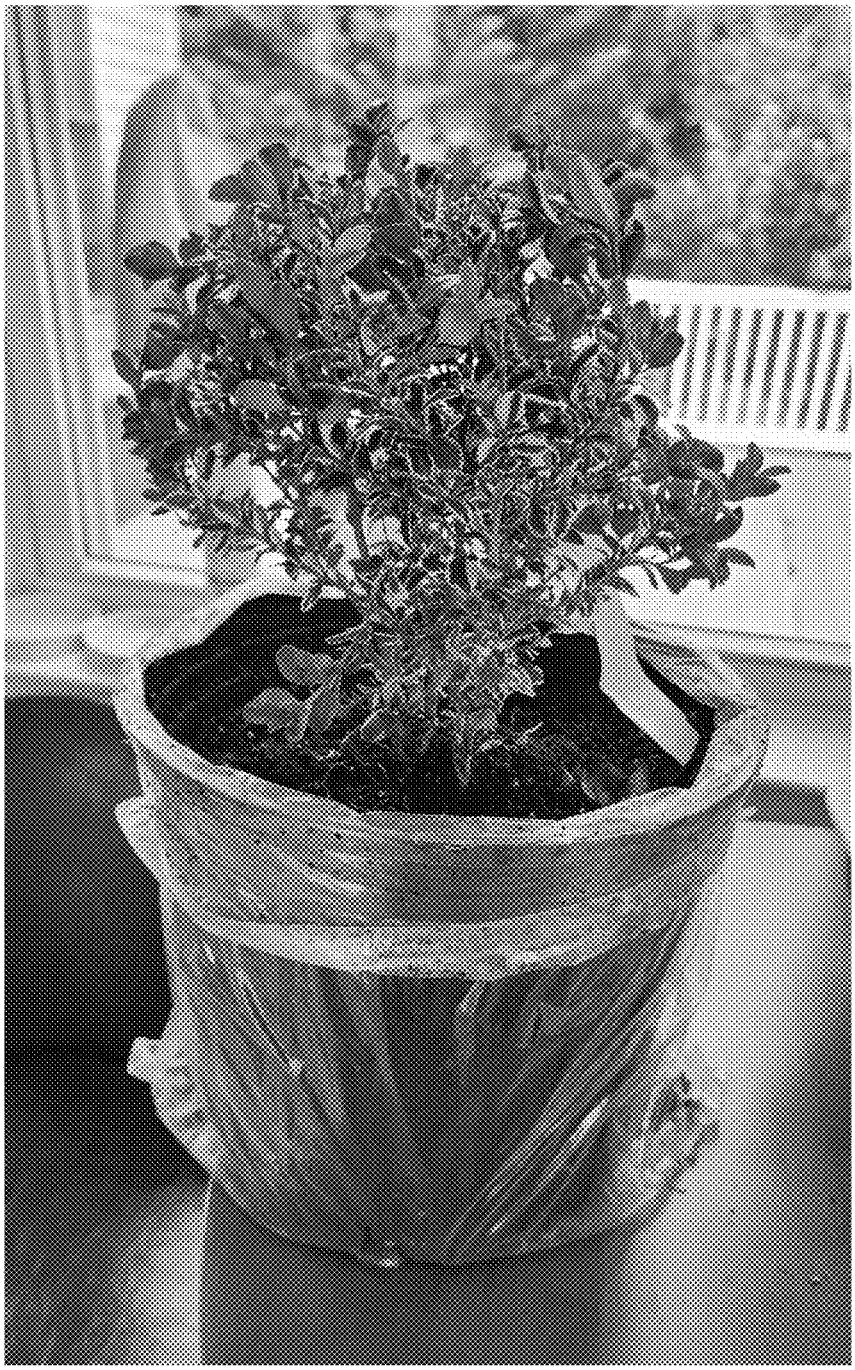

FIG. 1—illustrates a specimen of the plant displaying the overall growth and habit.

Figure 2:
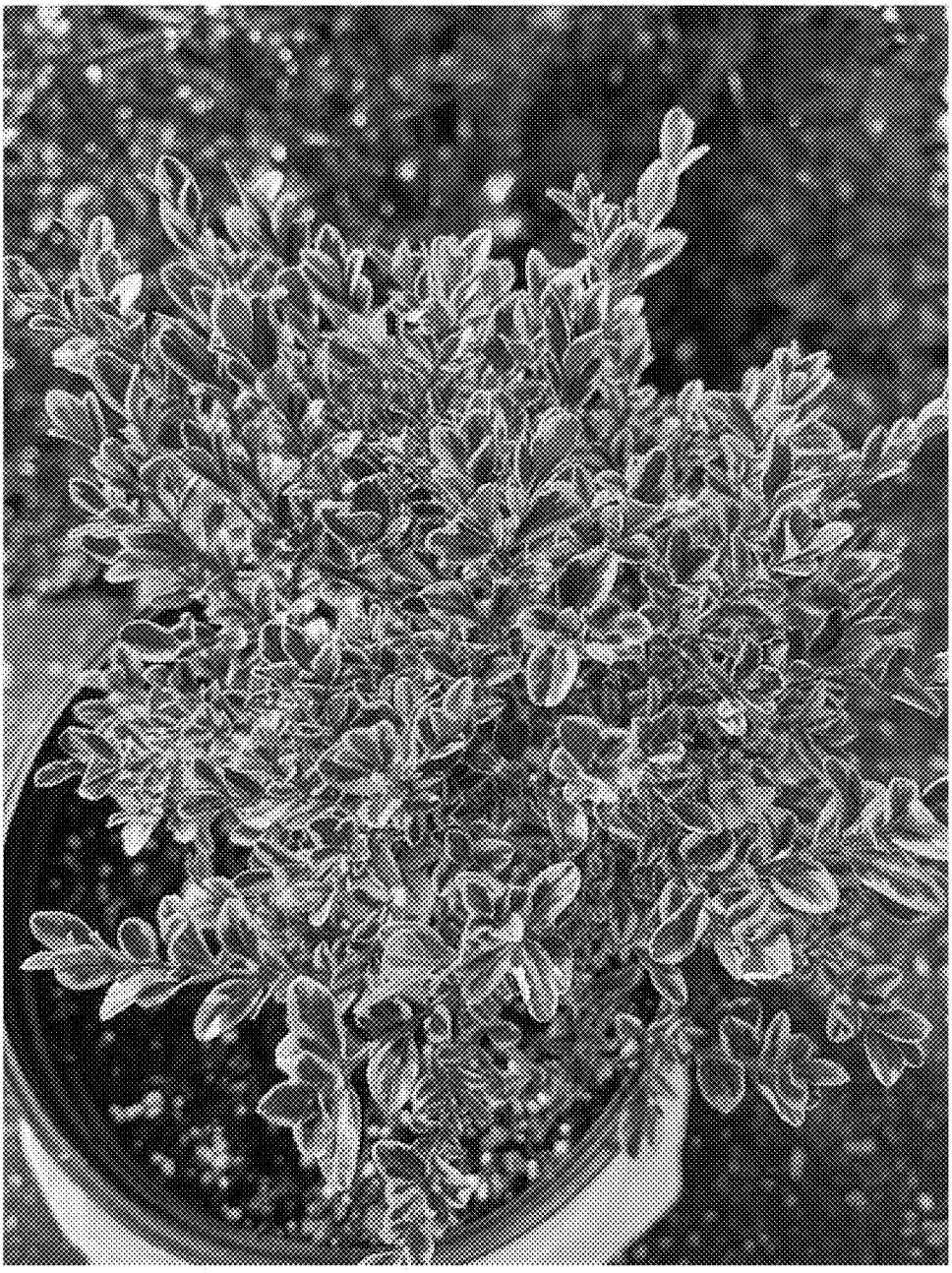

FIG. 2—illustrates a specimen of the plant in autumn displaying the overall growth and habit.

Figure 3:
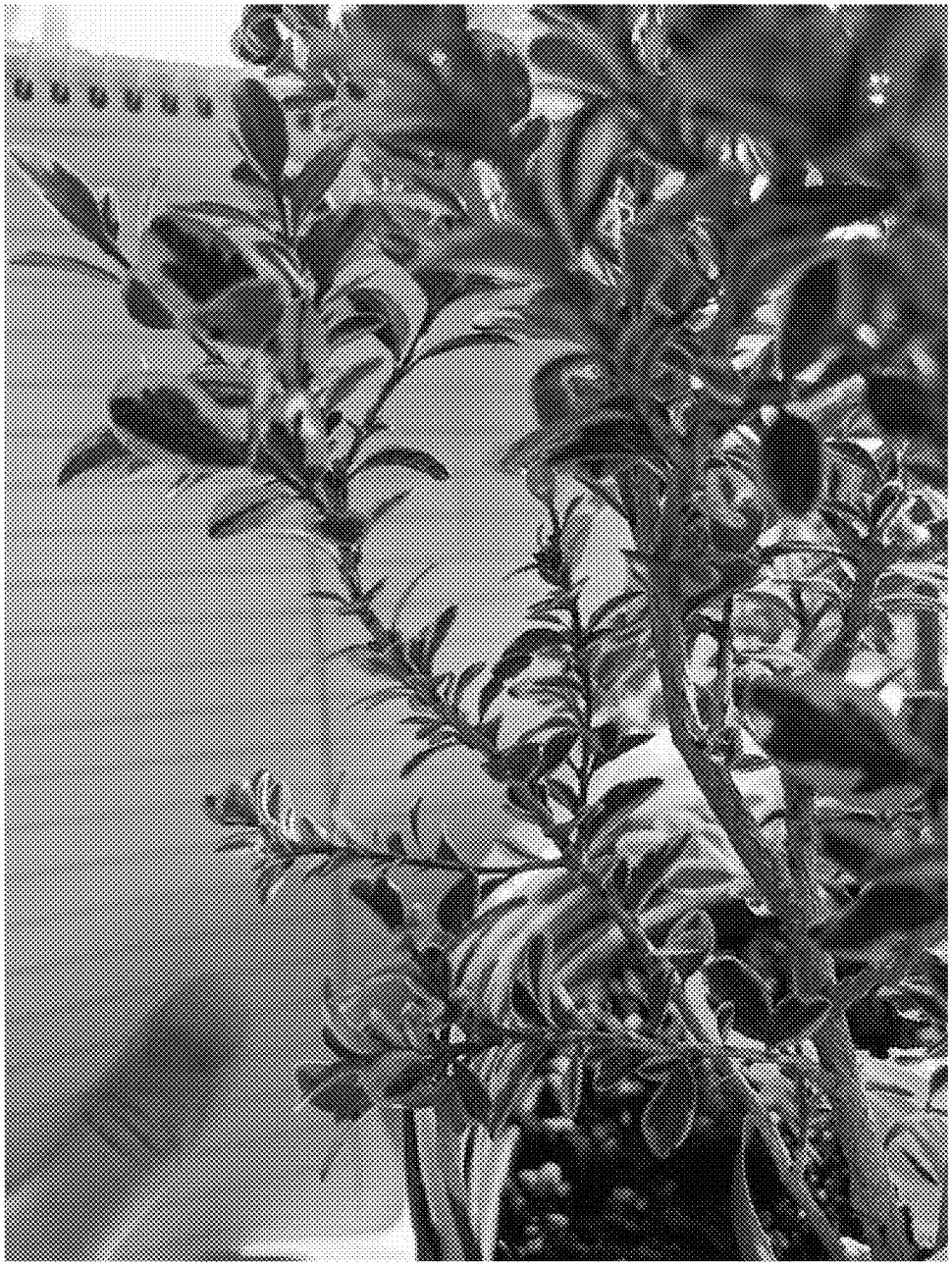

FIG. 3—illustrates a close-up view showing leaves on branches.

DETAILED BOTANICAL DESCRIPTION

The chart used in the identification of the colors is that of The Royal Horticultural Society (The R.H.S. Colour Chart), 2015 edition, London, England. The terminology which precedes reference to the chart has been added to indicate the corresponding color in more common terms and The R.H.S. Colour Chart designation used herein represents the closest color observed on the majority of the specified botanical feature. The color values were determined in May 2023 under natural light conditions in Wilmington, Delaware, except for the late autumn leaf color values which were determined in December 2024 under natural light conditions in Wilmington, Delaware. The description is based on the observation of plants approximately three and a half years of age growing in a 3-gallon container that was growing the past two years outdoors in Low Gap, North Carolina and pruned a couple months prior to observation. Measurements and numerical values represent averages of typical plants.

Botanical classification: *Buxus microphylla* cultivar 'TM108'.

Propagation:

*Type cutting*.—Terminal stem cuttings.

*Time to initiate roots during the fall*.—Approximately 60 days on average.

*Root description*.—Color is Greyed-Yellow Group 162C, fine, fibrous.

*Rooting habit*.—Light to moderate branching and density.

Plant:

*Habit*.—Evergreen shrub, upright, compact, rounded growth shape that is about as wide as it is tall.

*Commercial crop time*.—Approximately two years from a rooted cutting to finish in a 3-gallon pot on average.

*Size*.—Approximately 25.0 cm in height from soil level to top of plant plane on average; and approximately 23.0 cm in width on average.

*Growth rate*.—7 to 8 cm/year.

Branches:

*Branching habit*.—Upright stems arise from the base; lateral stems held in acute angles in opposite arrangement.

*Quantity of main branches per plant*.—Approximately 3 on average.

*Shape*.—Young stems are quadrangular; mature stems are round.

*Strength*.—Main stems are strong and rigid; secondary stems are moderately strong; tertiary stems are bendable.

*Size*.—Length: main stems are approximately 20.0 cm on average. — diameter: main stems are approximately 4.0 mm to 5.0 mm on average. — length of central internode: approximately 2.2 cm on average.

*Texture*.—Young stems: glabrous and smooth. — mature stems: woody, coarse, and somewhat ridged.

*Color*.—Young stems: Yellow-Green Group 144A. — mature stems: Greyed-Brown Group 199D.

Foliage:

*Number of leaves*.—Approximately 22 on average per lateral branch measuring 6.0 cm in length.

*Fragrance*.—Slight herbaceous scent when crushed.

*Form*.—Simple.

*Arrangement*.—Opposite, decussate.

Leaves:

*Shape*.—General: ovate. — margin: entire. — apex: rounded to retuse. — base: cuneate.

*Venation*.—Pattern: pinnate. — color: matches leaf surface.

*Size*.—Length of juvenile leaf: approximately 1.6 cm on average. — width of juvenile leaf: approximately 8.0 mm on average. — length of mature leaf: approximately 1.4 cm on average. — width of mature leaf: approximately 7.0 mm on average.

*Internode length*.—Approximately 8.0 mm on average.

*Texture*.—Upper and lower surfaces: leathery to smooth, slightly thick.

*Color*.—Upper surface of young foliage: variegated with a blend of Green Group 137A towards the center and Yellow-Green Group 144A towards the margin. — lower surface of young foliage: Yellow-Green Group 144B. — upper surface of mature foliage: variegated with a blend of Yellow-Green Group 147A towards the center and Greyed-Yellow Group 160A towards the margin. — lower surface of mature foliage: variegated with a blend of Yellow-Green Group 146B towards the center and Greyed-Yellow Group 160B towards the margin. — upper surface leaf late autumn color: variegated with a blend of Green Group 139A towards the center with margins varying from leaf to leaf, ranging from Yellow- Orange Group 22A, Yellow-Orange Group 20A, Yellow-Orange Group 16B and Orange Group 24A. — lower surface leaf late autumn color: variegated with a blend of Yellow-Green Group 146B towards the center with margins varying from leaf to leaf, ranging from Orange Group 24C, Yellow Group 14C, and Greyed-Orange Group 163C.

*Petiole*.—Length: approximately 1.0 mm on average. — width: approximately 1.0 mm on average. — texture: glabrous. — color: upper surface on young leaves is Yellow-Green Group 144A; lower surface on young leaves is Yellow-Green Group 144B; upper surface on mature leaves is Yellow-Green Group 147B; lower surface on mature leaves is Yellow-Green Group 146B.

Inflorescence: None observed to date.

Seed and fruit: None have been observed to date.

Development:

*Hardiness*.—Good cold hardiness in North Carolina; variety has grown well in Zone 6 in the mountains of Surry County, North Carolina.

*Tolerance to disease and pest*.—Very good resistance to boxwood blight (*Calonectria pseudonaviculata*).

The new 'TM108' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of boxwood plant named 'TM108' characterized by the following combination of characteristics:

(a) displays bright variegated leaf color, which is retained in the fall and winter, (b) resists winter foliar bronzing, (c) exhibits very good resistance to boxwood blight (*Calonectria pseudonaviculata*), and (d) provides a compact, rounded growth habit;

substantially as herein shown and described.

* * * * *